United States Patent [19]

Jørgensen

[11] Plant 4,411

[45] Apr. 24, 1979

[54] AFRICAN VIOLET

[76] Inventor: Frank Jørgensen, 5494 Stige, Denmark

[21] Appl. No.: 853,144

[22] Filed: Nov. 17, 1977

[30] Foreign Application Priority Data

Feb. 23, 1977 [DK] Denmark ..... 805/77

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Beveridge, DeGrandi, Kline & Lunsford

[57] ABSTRACT

A distinct and new variety of African violet plant distinguished by its large upstanding flowers of intense violet color with petals having entire margins which form a distinctive cluster at the center of the plant rising above a generally horizontal and rotate spread of large leaves having relatively short to half-long and thick petioles having a slender conical shape at their upper ends below the leaf.

3 Drawing Figures

BACKGROUND OF THE NEW PLANT VARIETY

The new variety of African violet plant was originated as a seedling produced by my crossing two African violet varieties selected from among my breeding stock at Stige, Denmark, with the objective of developing different and improved varieties suitable for the commercial market. The unusual and distinctive flower appearing on this plant and the unique, general compactness of its foliage caused me to select this plant for propagation and test. My asexual reproduction of this plant through several generations at Stige, Denmark by means of leaf cuttings, demonstrated that these unusual characteristics were firmly fixed, whereupon commercial propagation by leaf cuttings and division of shoots was begun and is now carried on at Stige, Denmark, the distinctive features of the new plant holding true from generation to generation.

DESCRIPTION OF THE DRAWING

The new variety of African violet plant is illustrated by the accompanying drawing which shows the form, growth habit, and color characteristics of the plant, the color reproduction being as nearly true as is reasonably possible to be had by conventional photographic procedures. The left-hand upper view shows the manner with which the flowers stand just above the compact surrounding foliage; the right-hand upper view is a close-up of a fully opened blossom of the new plant; and the lower view is taken downwardly from above the plant to show the compactness of the foliage.

DESCRIPTION OF THE NEW PLANT

The following is a detailed description of the new variety of African violet plant with color designations according to the Horticultural Colour Chart (HCC) produced by Robert F. Wilson for the British Colour Council and published by The Royal Horticultural Society at London, England.

THE PLANT

Origin: Seedling.

Parentage:

*Seed Parent.*—#16-2, an unnamed and unpatented variety in my breeding stock.

*Pollen Parent.*—#16-4, an unnamed and unpatented variety in my breeding stock.

Classification:

*Botanic.*—*Saintpaulia ionantha.*

*Commercial.*—Potted African violet.

Form: Very compact potted plant.

Height: About 10 cm from base (soil) to top of flowers and about 6 cm from base (soil) to top of foliage.

Growth: Vigorous and condensed with heavy petioles in rotate fashion holding leaves inclined upwardly so that they do not hang over the edge of the pot.

Foliage:

*Quantity.*—Rather sparse.

*Size of leaf.*—7 cm long and 7 cm wide, in the mature leaf.

*Shape of leaf.*—Circular with entire to slightly tongued margins. Wavy with ridges between the veins.

*Texture.*—Slightly tomentose.

*Veins.*—Pinnate — very pronounced on underside of leaf.

*Color.*—Upper side — Spinach Green 0960/1 with lighter Spinach Green 0960/3 edge zones and a central irregular oblong star-shaped Pea Green 61/2 spot of about 1 cm having its Sap Green 62/1 tips at some of the veins. Underside — Agathia Green 60/3 with Pea Green 61/2 veins.

*Petioles.*—4 cm long and 0.5 cm thick or more on mature leaf. The thick petioles extend conically to about double diameter at the upper end of the leaf. The petioles are Lilac Purple 031/1 and this color changes gradually over the upper conical part to the color of the under side of the leaf.

THE BUD

Form: Globular.

Size: 6 mm diameter, just before opening.

Opening rate: Very slow — six weeks from visible bud to fully opened flower.

Color: Spectrum Violet 735/3.

Sepals:

*Slender.*—Sepals star-shaped surround the bud.

*Number.*—5.

*Form.*—Spear-shaped and unbranched.

*Color.*—Inside — Fern Green 0862/3. Outside — Purple Madder 1028/2.

*Splitting.*—Calyx splits to star-shape.

*Aspect.*—Smooth on inside. Hairy on outside.

Peduncle: 9 cm long, erect, and of hairy aspect.

*Color.*—Purple Madder 1028/2.

THE FLOWER

Blooming Habit: Profuse and recurrent the year around.

Size: Large; about 4 cm in diameter.

Shape: Filled; low hemispheric like a rose or water lily.

Borne: The inflorescense is a cyme.

Petalage: Number — more than 25 arranged in several circular concentric rings, each ring having 5 petals of which two consecutive are a little smaller than the remaining.

*Form.*—Bulb-shaped with entire margins.

*Color.*—Topside of young flowers — Violet 36, of mature flowers Aster Violet 38. Reverse side — Spectrum Violet 735/3.

*Appearance.*—Velvety.

Peduncle: Sturdy, upright, about 9 cm long.

*Pedicels.*—About 2.5 cm long.

*Color.*—Purple Madder 1028/2.

Effect of Weather: Hot weather suppresses flowering and fades the color. The plant thrives in 70% to 90% humidity.

Fragrance: None.

Lasting Quality: 25–30 days for the fully opened flower.

Persistence: Flowers hang on and dry. Petals do not drop.

REPRODUCTIVE ORGANS

Stamens: No stamens or a few being imperfectly devoloped.

*Anthers.*—Each of the developed anthers is composed of two anther cells, basifixed in arrangement, and about 1.5 mm long.

*Color.*—Indian Yellow 6/1.

*Filaments.*—Length — about 3 mm. Color: Spectrum Violet 735/1, at top, White Green at the base.

*Pollen.*—Color — Light Yellow.

Pistils: One.

*Style.*—6 mm long. The style is often defectively developed or transformed into a petal.

*Stigma.*—Color — Spectrum Violet 735/1 in top and Mimosa Yellow 602/3 at base.

*Ovaries.*—Tomentose in the mature flower.

This new variety of African violet plant is particularly attractive as a house plant. It is vigorous in growth habit producing moderate foliage, situated in a dense rotate fashion, and rose or water lily like blossoms of intense violet color which form a distinctive upstanding cluster at the center of the plant. The profuse and year around recurrent blooming habit of this new variety also adds to its overall attractiveness and commercial value.

I claim:

1. A new variety of African violet plant, substantially as herein shown and described, characterized by the compact growth, the very filled intense violet upright flowers which rise upwardly in a central compact cluster above a circle of leaves having on the upper side a light central star-shaped spot and being supported by heavy peduncles increasing their diameter gradually towards the leaves.

* * * * *

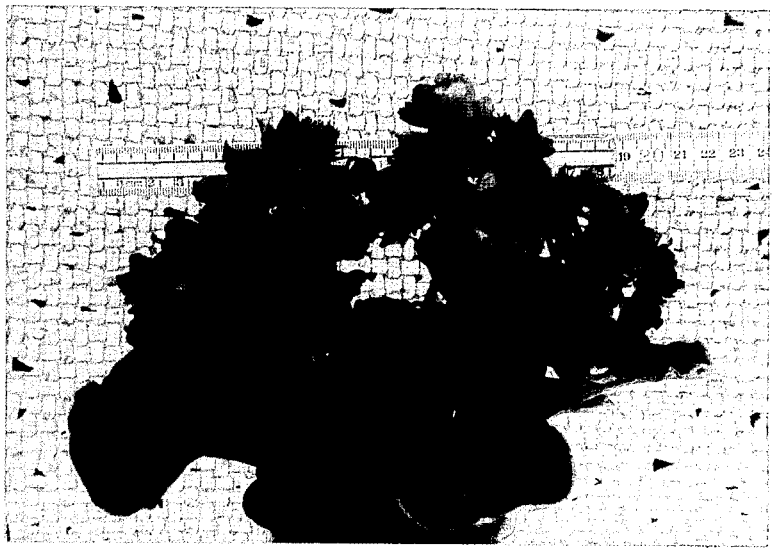
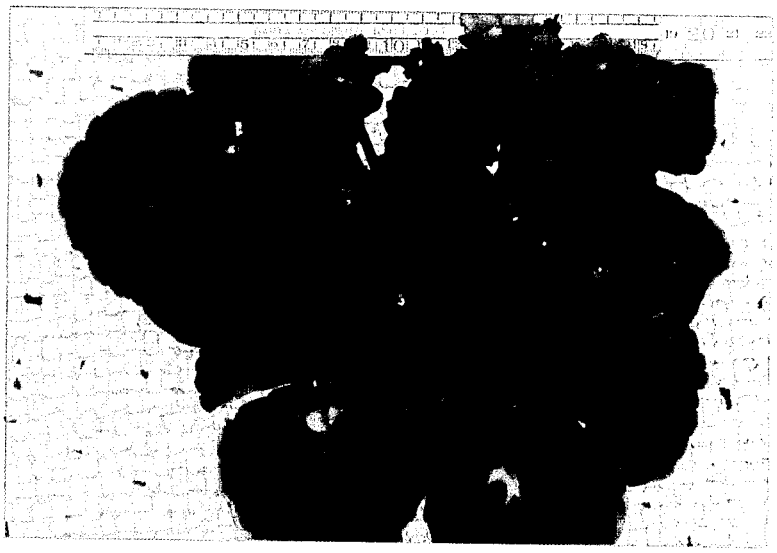

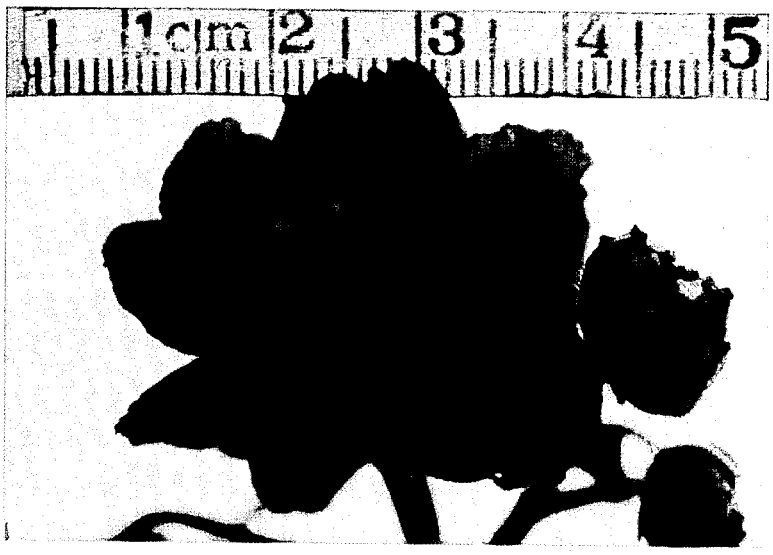
1 cm
2
3
4
5